US012734005B2

(12) United States Patent
Buhari et al.

(10) Patent No.: US 12,734,005 B2
(45) **Date of Patent: *Sep. 15, 2026**

(54) FINGER-WORN ORAL PROCEDURE APPARATUS AND METHOD

(71) Applicant: Cyrus Buhari, Stockton, CA (US)

(72) Inventors: Cyrus Buhari, Stockton, CA (US); Ryan Berg, Stockton, CA (US)

(73) Assignee: Dr. Cyrus Buhari, Stockton, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 18/740,774

(22) Filed: Jun. 12, 2024

(65) Prior Publication Data

US 2025/0049527 A1 Feb. 13, 2025

Related U.S. Application Data

(60) Continuation of application No. 17/345,250, filed on Jun. 11, 2021, now Pat. No. 12,011,247, which is a (Continued)

(51) Int. Cl.
*A61B 42/20* (2016.01)
*A41D 13/08* (2006.01)
*A61D 15/00* (2006.01)

(52) U.S. Cl.
CPC ............ *A61B 42/20* (2016.02); *A41D 13/087* (2013.01); *A61D 15/00* (2013.01)

(58) Field of Classification Search
CPC ........ A61B 42/20; A61B 1/24; A41D 13/087; A61D 15/00; A61C 5/14
(Continued)

(56) References Cited

U.S. PATENT DOCUMENTS 2,434,317 A 1/1948 Gross
3,343,177 A 9/1967 Bellamy
(Continued)

FOREIGN PATENT DOCUMENTS

WO WO-9418902 A1 * 9/1994 ............... A61C 5/90
WO WO-03045444 A2 * 6/2003 ............. A61B 42/00

OTHER PUBLICATIONS

Reinold Josef Dr, Toothbrush worn on user's fingertip, DE-19506789-C1 (Year: 1996).*

(Continued)

*Primary Examiner* — Eric J Rosen
*Assistant Examiner* — Mirayda A Aponte
(74) *Attorney, Agent, or Firm* — Schwegman Lundberg & Woessner, P.A.

(57) ABSTRACT

A device and methods for making and using an oral procedure apparatus include a tubular member and a flange. The tubular member forms a lumen extending from a first end of the tubular member to a second end of the tubular member, the lumen having a lumen cross-section sized to admit a human finger extending through the lumen, the tubular member having a tubular cross-section sized to be admitted into a mouth of a patient, the tubular member formed from a material substantially resilient against a bite from the mouth of the patient. The flange is coupled to the first end of the tubular member, the flange having a flange cross-section sized larger than the mouth of the patient.

18 Claims, 6 Drawing Sheets

Related U.S. Application Data division of application No. 14/984,979, filed on Dec. 30, 2015, now Pat. No. 11,033,349.

(60) Provisional application No. 62/097,796, filed on Dec. 30, 2014.

(58) Field of Classification Search
USPC .............................................. 433/33; 119/600
See application file for complete search history.

(56) References Cited

U.S. PATENT DOCUMENTS

| | | | | |
|---|---|---|---|---|
| 3,544,020 | A | 12/1970 | Goldberg et al. | |
| 5,363,864 | A | 11/1994 | Kaiser | |
| 6,839,905 | B1 * | 1/2005 | Bruder | A41D 13/087 2/21 |
| 11,033,349 | B2 * | 6/2021 | Buhari | A41D 13/087 |
| 12,011,247 | B2 * | 6/2024 | Buhari | A61B 42/20 |
| 2005/0268369 | A1 | 12/2005 | Santiago | |
| 2010/0119989 | A1 * | 5/2010 | Raybuck | A61C 5/90 264/16 |
| 2013/0203013 | A1 | 8/2013 | Taddeo et al. | |
| 2013/0245687 | A1 * | 9/2013 | Bachmann | A61J 17/02 606/235 |
| 2016/0184042 | A1 | 6/2016 | Buhari et al. | |
| 2021/0298859 | A1 | 9/2021 | Buhari et al. | |

OTHER PUBLICATIONS

"U.S. Appl. No. 14/984,979, 312 Amendment filed Jul. 24, 2019", 4 pgs.

"U.S. Appl. No. 14/984,979, Advisory Action mailed Aug. 13, 2019", 3 pgs.

"U.S. Appl. No. 14/984,979, Appeal Brief filed Jul. 24, 2019", 19 pgs.

"U.S. Appl. No. 14/984,979, Final Office Action mailed Jan. 24, 2019", 12 Pgs.

"U.S. Appl. No. 14/984,979, Non Final Office Action mailed May 17, 2018", 15 pgs.

"U.S. Appl. No. 14/984,979, Non Final Office Action mailed Jul. 10, 2020", 11 pgs.

"U.S. Appl. No. 14/984,979, Notice of Allowance mailed Feb. 18, 2021", 8 pgs.

"U.S. Appl. No. 14/984,979, Notification of Non-Compliant Appeal Brief mailed Aug. 13, 2019", 2 pgs.

"U.S. Appl. No. 14/984,979, Response filed Jan. 8, 2018 to Restriction Requirement mailed Oct. 6, 2017", 5 pgs.

"U.S. Appl. No. 14/984,979, Response filed Aug. 17, 2018 to Non-Final Office Action mailed May 17, 2018", 8 pgs.

"U.S. Appl. No. 14/984,979, Response filed Oct. 12, 2020 to Non Final Office Action mailed Jul. 10, 2020", 10 pgs.

"U.S. Appl. No. 14/984,979, Restriction Requirement mailed Oct. 6, 2017", 7 pgs.

"U.S. Appl. No. 14/984,979, Supplemental Amendment filed Sep. 13, 2019", 5 pgs.

"U.S. Appl. No. 17/345,250, Non Final Office Action mailed May 24, 2023", 12 pgs.

"U.S. Appl. No. 17/345,250, Notice of Allowance mailed Feb. 12, 2024", 7 pgs.

"U.S. Appl. No. 17/345,250, Response filed Aug. 24, 2023 to Non Final Office Action mailed May 24, 2023", 8 pgs.

* cited by examiner

FINGER-WORN ORAL PROCEDURE APPARATUS AND METHOD

PRIORITY

The application is a continuation of U.S. patent application Ser. No. 17/345,250, filed Jun. 11, 2021, which is a division of U.S. patent application Ser. No. 14/984,979, filed Dec. 30, 2015, which claims the benefit of U.S. Provisional No. 62/097,796, filed Dec. 30, 2014, all of which are incorporated herein by reference in their entirety.

TECHNICAL FIELD

The disclosure herein relates generally to a finger-worn oral procedure apparatus and method.

BACKGROUND

Certain patients undergoing oral procedures or examinations may be prone to biting down during the procedure or examination, particularly where the patient does not have full control over their jaw muscles. A patient who is, for instance, disabled or under anesthesia may pose a threat of a bite wound to a medical professional during the procedure or examination. Bite blocks have previously been developed that may be inserted into the patient's mouth to inhibit biting. An opening in the bite block may allow for equipment to be moved in and out of the moth and oropharynx. Certain bite blocks may be directed and configured more toward protecting other equipment used in the procedure than the finger or hand of the medical professional.

DESCRIPTION OF THE EMBODIMENTS

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

Bite blocks described above may not facilitate passage of equipment into the esophagus. A finger may still be needed to guide the equipment to stay in the midline towards the esophagus. Such bite blocks may merely protect the equipment from damage. Such bite blocks may have side ports for insertion of a finger or suction device but this opening may be small and not protective of bites.

Further, such bite blocks may not be inserted into the mouth of a patient who has an endotracheal tube in place, as may be the case in a critical care setting. There may not be enough space with the other tubes in place to put a large bite block. Additionally, there are times when it may be necessary for a physician to palpate the back of a patient's throat to palpate or feel tonsils, adenoids, teeth, uvula, and so forth. While sedation may not be utilized for such simple procedures, there may remain risk to the physician or examiner of being bitten. This also applies to veterinary examinations of dogs in particular. A conventional bite block may be impractical for this purpose in both cases.

An oral procedure apparatus has been developed that may be worn on the finger of the medical professional, in contrast with conventional bite blocks which are inserted into and secure the patient's mouth and through which fingers and implements are then passed through and removed while the bite block remains in the patient's mouth. The oral procedure apparatus, or "finger-worn bite block", may be made of materials resilient enough to prevent the compressive force of a bite from injuring the finger around which the bite block is being worn but accommodating enough not to damage the teeth of the patient. The oral procedure apparatus may include a flange configured to prevent the oral procedure apparatus from embolizing into the mouth of the patient. A flare in the oral procedure apparatus may guide, direct, or other accommodate the teeth of the patient into a groove or channel in such a fashion that may reduce a likelihood of the patient's teeth from slipping off of the end of the oral procedure apparatus. The length of the oral procedure apparatus may allow for flexibility in the distal phalanges of the medical professional's finger for natural movement of the finger in the mouth, such as by being sized to fit between joints. The bite block may be sized to leave open space in the mouth for the passage of equipment such as probes or scopes without the need of a traditional bite block.

Figure 1:
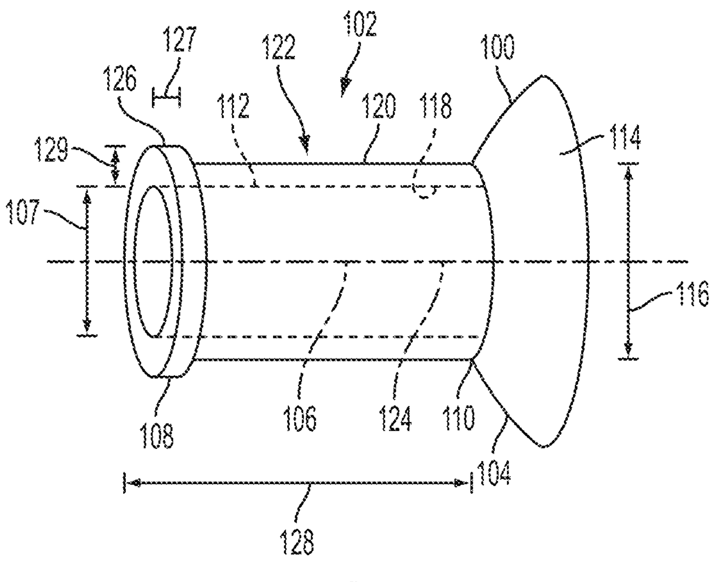
FIG. 1 is an image of an oral procedure apparatus, in an example embodiment.

FIG. 1 is an image of an oral procedure apparatus 100, in an example embodiment. The oral procedure apparatus 100 may also be known as a "finger-worn bite block". The oral procedure apparatus 100 includes a tubular member 102 and a flange 104.

As illustrated, the tubular member 102 forms a lumen 106 extending axially from a first end 108 of the tubular member 102 to a second end 110 of the tubular member 102. The tubular member 102 is sized and shaped to admit a finger of a medical professional within and through the lumen 106. A medical professional may be understood to be any person who may perform or participate in an oral procedure or operation in or on a patient. A patient may be human or animal, including but not necessarily limited to house pets, such as dogs, cats, and the like.

As illustrated, the lumen 106 has a circular cross-section 107. However, the lumen 106 may, in various examples, have alternative cross-sections 107 that may be suitable to admit a human finger. In various examples, the lumen 106 has an oval cross-section 107 or an irregular cross-section 107.

The lumen 106, and the tubular member 102 and the oral procedure apparatus 100 generally, may be sized according to conventional finger sizes. Multiple different sizes of oral procedure apparatuses 100 may be formed for specific sizes of individual medical professional fingers. In various examples, lumens 106 with circular cross-sections 107 may have diameters ranging from approximately 13.3 millimeters to approximately 25.0 millimeters. The sizes may correspond to conventional finger ring sizes and/or glove sizes. Thus, oral procedure apparatus 100 may be sized according to increments of one-half ring sizes ranging from size three (3) to size 15.5.

A medical professional may obtain a suitable oral procedure apparatus 100 based on the medical professional's own ring and/or glove size. The ring size of the medical professional may be measured according to whatever finger the medical professional intends to wear the oral procedure apparatus 100 over, such as an index finger. In various examples, the medical professional may be advised to obtain an oral procedure apparatus 100 that is one-half size larger than the medical professional's ring or glove size to facilitate the wearing of a surgical glove or other protective mechanism or allow the wearer's finger to flex or bend at a joint within the tubular member.

As further illustrated, the tubular member 102 is cylindrical in accordance with the circular cross-section 107 of the lumen 106. In such an example, the tubular member 102 is a complete cylinder without gaps or slots. However, in alternative examples, the tubular member 102 is not necessarily cylindrical, such as to form lumens 106 having cross-sections 107 that are not circular. In various examples, the tubular member 102 further may not fully enclose the lumen 106, such as by incorporating slots or gaps in the material 112 that makes up the tubular member 102 but which nevertheless define a lumen 106 that can admit a human finger.

The tubular member 102 may have a tubular member cross-section 116 sized to be admitted in a mouth of the patient. The tubular member 102 cross-section 116 may be a function of a thickness of the material 112 and the cross-section 107 of the lumen. Alternatively, the thickness of the material 112 may be driven, at least in part, by a need to have the cross-section 116 of the tubular member 102 such that the tubular member 102 may fit within a mouth of the patient.

In various examples, the oral procedure apparatus 100 is formed from a single, or monolithic, piece of material 112, such as a medical-grade, biocompatible hard polymer, formed into the tubular member 102 and the flange 104, such as by injection molding or other suitable method. Additionally or alternatively, the tubular member 102 and the flange 104 may be formed separately and coupled together. In such an example, the tubular member 102 and the flange 104 may be formed of different materials. In an example, at least the tubular member 102 may be formed of a material 112 having a hardness that is sufficiently resilient against deformation so as to protect the finger of a medical professional against compressive force injury if the patient bites down while the oral procedure apparatus 100 is inserted in the mouth of the patient but not so hard as to cause injury to the teeth of the patient if the patient bites down on the tubular member 102. The tubular member 102 may be sufficiently rigid that it is difficult or impossible for a wearer of the apparatus 100 to bend their finger when inserted within the tubular member 102, which may promote the sizing of the tubular member 102 to fit between joints. In an example, the flange 104 is formed from the same material 112 as the tubular member 102 or a different material 114 as the tubular member 102 that does not necessarily meet the hardness characteristics of the material 112 used to form the tubular member 102.

In an example, the tubular member 102 is formed of a material 112 that is a medical grade plastic. In various examples, the medical grade plastic may comply with contemporary and/or future requirements or recommendations of some or all of the Food and Drug Administration, the United States Pharmacopeial Convention, and other regulatory or advisory bodies. In an example, the material 112 has a hardness of between approximately Shore durometer A 70 and Shore durometer D 80.

The material 112 of the tubular member 102 has an inner surface 118 facing the lumen 106 and an outer surface 120 opposite the inner surface 118. The outer surface 120 may have or may form a channel 122 sized and configured to seat the teeth of the patient. The channel 122 may be circumferential and extend around the outer surface 120 of the tubular member 102. The channel 122 may be orthogonal to a primary axis 124 of the lumen 106 and the tubular member 102 generally and/or otherwise generally circumferential about the tubular member 102.

The channel 122 may be formed by and defined between a generally radially extending ridge 126 proximate the second end 110 and the generally radially extending flange 104 proximate the first end 108. In various examples, the ridge 126 may have a width 127 based on the buccolabial dimensions of human teeth, in various examples between approximately six (6) millimeters and approximately twelve (12) millimeters, to facilitate the accommodation of teeth, as described herein. In various examples, the ridge 126 has a depth 129 in the range from approximately one (1) millimeter to approximately five (5) millimeters, again to facilitate the accommodation of teeth. Various examples of the oral procedure apparatus 100 may incorporate dimensions of the ridge 126 outside of the ranges listed here and such dimensions may be selected based on the characteristics of the patient in which the oral procedure apparatus 100 is to be used.

The tubular member 102 may be sized according to typical finger anatomy. In an example, and as will be illustrated herein, the tubular member 102 may be sized in diameter to fit over a proximal phalange of a human finger and may be sized in length to fit between a metacarpophalangeal (MCP) joint and proximal inter-phalangeal (PIP) joint of the finger. In an example, the tubular member has a length 128 of approximately twenty (20) millimeters.

The flange 104 may help prevent the oral procedure apparatus 100 from embolizing into the mouth of the patient. The flange 104 may be sized and shaped to be larger than the mouth of a typical patient. While the flange 104 is depicted as being generally circular, the flange 104 may be oval, rectangular, or irregularly shaped, among any of a variety of shapes. In various examples, oral procedure apparatuses 100 may have variously sized flanges to accommodate different patient mouth sizes and shapes. Thus, oral procedure apparatuses 100 may be built with multiple individually selectable characteristics based on the characteristics of the medical professional and the patient, including, but not limited to, lumen 106 diameter, tubular member length 128, flange 104 size and shape, and so forth. In various examples, the flange 104 has a diameter of approximately four (4) to approximately five (5) centimeters, though alternative diameter sizes are contemplated. The flange 104 may form an angle relative to the primary axis 124 and/or to the outer surface of approximately seventy (70) degrees. In various examples, the flange 104 forms a substantially conic shape or cross-section with generally straight sides or forms a cup shape with curved or parabolic sides.

Figure 2A:
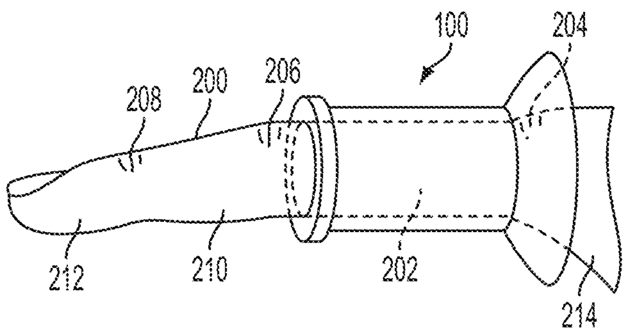
FIGS. 2A and 2B are images of an oral procedure apparatus as placed on a human finger, in an example embodiment.
Figure 2B:
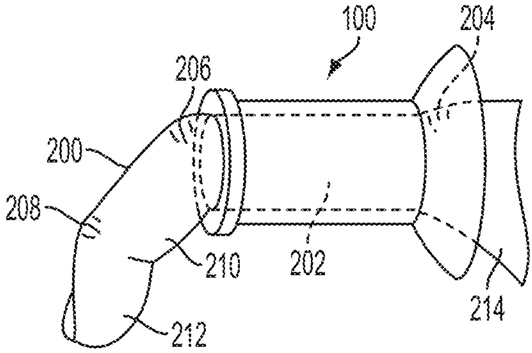

FIGS. 2A and 2B are images of the oral procedure apparatus 100 as placed on a human finger 200, in an example embodiment. The oral procedure apparatus 100 is placed so that the proximal phalange 202 extends through the lumen 106. As illustrated, the tubular member 102 is between the MCP joint 204 and the PIP joint 206. Such positioning may allow for the joints 206, 208 to bend freely. However, it is to be understood that various uses of the oral procedure apparatus 100 may result in one or both of the joints 206, 208 being obstructed without substantially reducing the utility of the oral procedure apparatus 100.

The positioning of the oral procedure apparatus 100 allows for the finger 200 to flex and bend, as illustrated between FIGS. 2A and 2B. In FIG. 2A the finger 200 is substantially straight while in FIG. 2B the finger 200 is bent. The positioning of the oral procedure apparatus 100 may not inhibit the bending of the finger as illustrated in FIG. 2B.

As depicted, the flange 104 is proximate the MCP joint 204. The flange 104 may extend over the MCP joint 204 at least in part in order to allow as much of the finger 200 to be extended in the mouth of the patient as possible or practical. The flange 104 may be sized and shaped so as to not inhibit movement of the MCP joint 204.

The oral procedure apparatus 100 may be positioned at any of a variety of locations on the finger 200. In various examples, the oral procedure apparatus 100 may be positioned so that the tubular member 102 does not overlap any of the MCP joint 204, the PIP joint 206, or the distal inter-phalangeal (DIP) joint 208 so as not to inhibit movement of those joints 204, 206, 208. As noted above, however, the oral procedure apparatus 100 may be positioned in a way that inhibits the movement of one or more of those joints 204, 206, 208 while still maintaining some or all of the effectiveness of oral procedure apparatus 100. The tubular member 102 may generally be positioned along one of the proximal phalange 202, the middle phalange 210, or the distal phalange 212, or may cover two or more of the phalanges 202, 210, 212 if one or more of the joints 204, 206, 208 are obstructed by the oral procedure apparatus 100. The flange 104 may extend at least partially over the hand 214 of the medical professional.

Figure 3A:
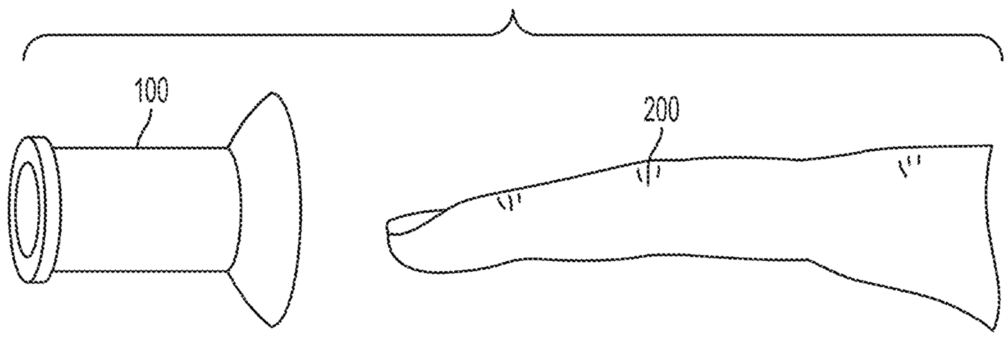
FIGS. 3A-3C sequentially illustrate the placement of an oral procedure apparatus on a finger and the subsequent use thereof in the mouth of a patient, in an example embodiment.
Figure 3B:
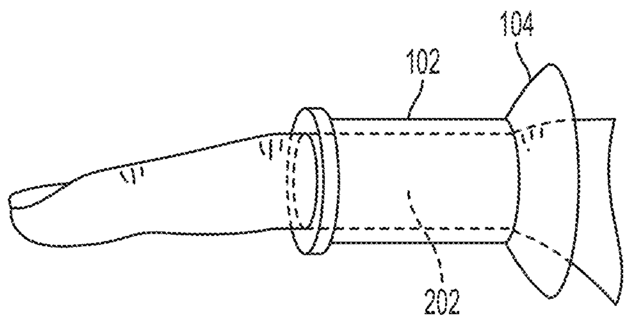
Figure 3C:
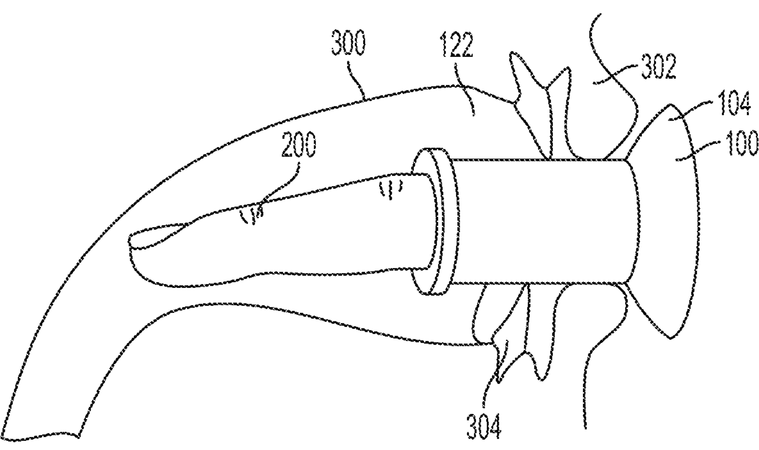

FIGS. 3A-3C sequentially illustrate the placement of an oral procedure apparatus 100 on a finger 200 and the subsequent use thereof in the mouth 300 of a patient 302, in an example embodiment. While this particular use case is illustrated, it is to be recognized and understood that the oral procedure apparatus 100 may be utilized according to or for any of a variety of uses that are not explicitly illustrated here.

In FIG. 3A, the oral procedure apparatus 100 is held or otherwise positioned in relation to the finger 200. In FIG. 3B, the oral procedure apparatus 100 slides over the finger 200 such that the flange 104 is proximate the MCP joint 204 and the tubular member 102 fits over the proximal phalange 202. In FIG. 3C, the finger 200, with the oral procedure apparatus 100 placed thereon, is inserted in the mouth 300 of the patient 302. The size and shape of the flange 104, being larger than the mouth 300 of the patient 302, prevents the flange 104 and the oral procedure apparatus 100 generally from embolizing into the mouth 300 of the patient 302. The patient's teeth 304 may be seated in the channel 122 to limit movement of the oral procedure apparatus 100 relative to the teeth 304 and the mouth 300 generally. The size of the tubular member 102 may further facilitate the movement of the apparatus 100 from side-to-side within the mouth of the patient. The medical professional may rotate the finger 200 and manipulate the joints 204, 206, 208 of the finger 200 in order to facilitate or conduct an oral procedure in the mouth 300.

Figure 4A:
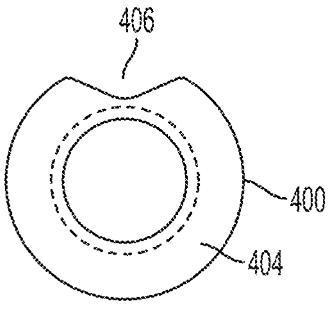
FIGS. 4A and 4B are end-on and side profiles, respectively, of an oral procedure apparatus, in an example embodiment.
Figure 4B:
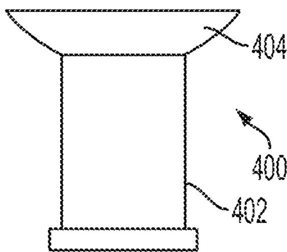

FIGS. 4A and 4B are end-on and side profiles, respectively, of an oral procedure apparatus 400, in an example embodiment. The oral procedure apparatus 400 may incorporate or be made or formed from the same or similar materials as the oral procedure apparatus 100 and may be utilized in the same or similar manner as the oral procedure apparatus 100. As such, the oral procedure apparatus 400 includes a tubular member 402 and a flange 404 that may be sized and function in the same or similar manner to that of the tubular member 102 and the flange 104.

The flange 404 incorporates a notch 406 that is configured to admit the webbing between adjacent fingers of a hand, an adjacent finger, an ornament, such as a ring, or other type of object or jewelry worn on an adjacent finger, or any other biological or artificial obstruction that may interfere with the flange 404 and the placement of the oral procedure apparatus 400 generally. The notch 406 may be formed as part of the process of making the flange 404 or may be cut out of the flange 404 at a later time. As illustrated, the notch 406 defines an arc along or around the circumference of the flange 404. However, it is to be understood that the notch 406 may have any suitable size, shape, or general configuration.

Figure 5:
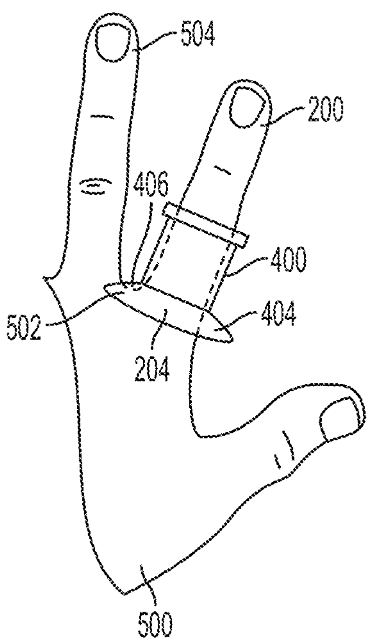
FIG. 5 is an image of an oral procedure apparatus on a human hand, in an example embodiment

FIG. 5 is an image of the oral procedure apparatus 400 on a human hand 500, in an example embodiment. As depicted, the flange 404 is proximate the MCP joint 204. The notch 406 admits webbing 502 of the hand 500 between the index finger 200 and the middle finger 504, thereby allowing the oral procedure apparatus 400 to be seated in close proximity to the MCP joint 204. The flange 404 may extend over the MCP joint 204 at least in part in order to allow as much of the finger 200 to be extended in the mouth of the patient as possible or practical. The flange 404 may be sized and shaped so as to not inhibit movement of the MCP joint 204.

Flowcharts

Figure 6:
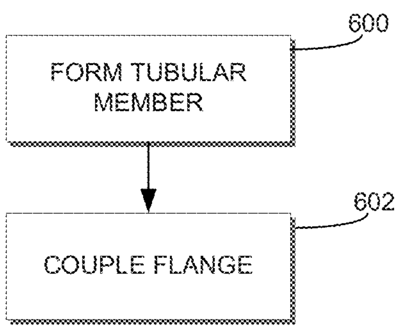
FIG. 6 is a flowchart for making an oral procedure apparatus, in an example embodiment.

FIG. 6 is a flowchart for making an oral procedure apparatus 100, in an example embodiment. While the flowchart is detailed in relation to the oral procedure apparatus 100 disclosed herein, it is to be understood that the flowchart may be applied to any applicable oral apparatus or device generally.

At 600, a tubular member is formed, the tubular member forming a lumen extending from a first end of the tubular member to a second end of the tubular member, the lumen having a lumen cross-section sized to admit a human finger extending through the lumen, the tubular member having a tubular cross-section sized to be admitted into a mouth of a patient, the tubular member formed from a material substantially resilient against a bite from the mouth of the patient. In an example, the tubular member is formed from a polymer. In an example, the polymer has a hardness between approximately Shore durometer A 70 and Shore durometer D 80.

In an example, the tubular member has an inner surface facing the lumen and an outer surface opposite the inner surface, wherein the tubular member forms a channel on the outer surface, the channel substantially orthogonal to a primary axis of the lumen, the channel configured to seat teeth of the patient. In an example, the channel is circumferential about the tubular member.

In an example, the tubular member has a tubular length from the first end to the second end selected to be less than a phalange length of a proximal phalange of the human finger. In an example, the tubular length is approximately twenty (20) millimeters. In an example, the tubular member is cylindrical. In an example, the tubular member is a complete cylinder extending from the first end to the second end.

At 602, a flange is coupled to the first end of the tubular member, the flange having a flange cross-section sized larger than the mouth of the patient. In an example, the tubular member and the flange are formed from a single piece of material. In an example, the flange is notched by removing material from the flange.

Figure 7:
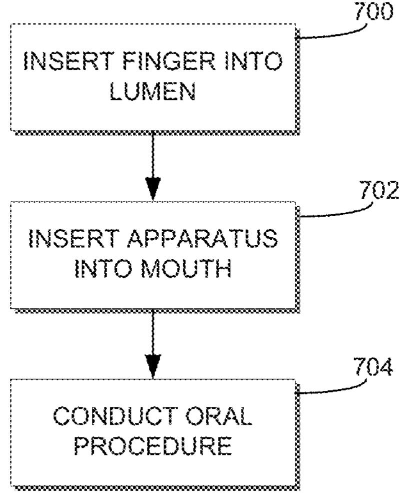
FIG. 7 is a flowchart for using an oral procedure apparatus, in an example embodiment.

FIG. 7 is a flowchart for using an oral procedure apparatus 100, in an example embodiment. While the flowchart is detailed in relation to the oral procedure apparatus 100 disclosed herein, it is to be understood that the flowchart may be applied to any applicable oral apparatus or device generally.

At 700, a finger of a medical professional is inserted into a lumen of an oral procedure apparatus, the oral procedure apparatus including a tubular member and a flange, the tubular member forming a lumen extending from a first end of the tubular member to a second end of the tubular member, the lumen having a lumen cross-section sized to admit a human finger extending through the lumen, the tubular member having a tubular cross-section sized to be admitted into a mouth of a patient, the tubular member formed from a material substantially resilient against a bite from the mouth of the patient, the flange coupled to the first end of the tubular member, the flange having a flange cross-section sized larger than the mouth of the patient. In an example, the tubular member has an inner surface facing the lumen and an outer surface opposite the inner surface, wherein the tubular member forms a channel on the outer surface, the channel substantially orthogonal to a primary axis of the lumen, further comprising seating the teeth of the patient in the channel. In an example, the channel is circumferential about the tubular member.

At 702, the oral procedure apparatus is inserted into the mouth of a patient.

At 704, an oral procedure is conducted on the patient with the finger of the medical professional as inserted into the lumen. The conduction of the oral procedure may optionally include the insertion of an instrument alongside the oral procedure apparatus during the procedure and/or the movement of the oral procedure apparatus within the mouth, including the lateral or side-to-side movement of the oral procedure apparatus.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An oral procedure apparatus configured to be placed over a finger of a wearer and partially admitted into a mouth of a patient, comprising:

a tubular member forming a lumen having a lumen cross-section sized to admit the finger of the wearer extending through the lumen, the tubular member having a circular cross-section configured to be admitted into the mouth of a patient and configured to be seated between a metacarpophalangeal (MCP) joint and up to a proximal inter-phalangeal (PIP) joint of the finger of the wearer, the tubular member having a hardness between Shore durometer A 70 and Shore durometer D 80; and a flange having an inner surface and an outer surface configured to be adjacent to a knuckle of the wearer, the flange having a first flange end and a second flange end, the first flange end positioned to a first end of the tubular member and having a first width, the second flange end having a second width larger than the first width, wherein a flange cross-section is configured to be larger than the mouth of the patient.

2. The oral procedure apparatus of claim 1, wherein the tubular member has an inner surface facing the lumen and an outer surface opposite the inner surface, wherein the tubular member forms a channel on the outer surface, the channel orthogonal to a primary axis of the lumen.

3. The oral procedure apparatus of claim 2, wherein the channel is circumferential around the tubular member is configured to seat a tooth of the patient anywhere around the channel.

4. The oral procedure apparatus of claim 3, wherein the channel is formed between a radially extending ridge proximate a second end of the tubular member and the flange proximate the first end and wherein the flange is configured to be positioned proximate the knuckle of the wearer.

5. The oral procedure apparatus of claim 4, wherein the radially extending ridge has a width of between six and twelve millimeters.

6. The oral procedure apparatus of claim 5, wherein the radially extending ridge has a depth of between one and five millimeters.

7. The oral procedure apparatus of claim 1, wherein the tubular member has a tubular length from a first end to a second end of the tubular member configured to be less than a phalange length of a proximal phalange of the finger of the wearer.

8. The oral procedure apparatus of claim 1, wherein the tubular member is cylindrical.

9. The oral procedure apparatus of claim 8, wherein the tubular member is a complete cylinder extending from a first end to a second end of the tubular member.

10. The oral procedure apparatus of claim 1, wherein the tubular member and the flange are formed from a single piece of material.

11. The oral procedure apparatus of claim 1, wherein the flange forms a notch, the notch defining an arc around a portion of a circumference of the flange, and wherein placing the oral procedure apparatus on the finger of the wearer includes admitting webbing of a hand of the wearer adjacent to the finger of the wearer into the notch.

12. The oral procedure apparatus of claim 11, wherein:
the outer surface of the flange is parabolic;
the inner surface of the flange is parabolic; and
placing the oral procedure apparatus on the finger of the wearer includes placing the inner surface of the flange around the knuckle of the wearer.

13. The oral procedure apparatus of claim 11, wherein the outer surface of the flange is a straight outer surface.

14. The oral procedure apparatus of claim 11, wherein the outer surface of the flange is conical and the inner surface of the flange is conical.

15. The oral procedure apparatus of claim 1, wherein the outer surface of the flange is concave and wherein the inner surface of the flange is convex.

16. A method of using an oral procedure apparatus comprising a tubular member extending from a first end to a second end, the method comprising:
placing the oral procedure apparatus over a finger of a wearer so that the first end is positioned proximate a metacarpophalangeal (MCP) joint of the wearer;
inserting the second end of the tubular member and the finger into a mouth of a patient;
seating at least one tooth of the patient onto the tubular member so that a flange of the oral procedure apparatus prevents the oral procedure apparatus from embolizing into the mouth of the patient; and
bending the finger at a proximal inter-phalangeal (PIP) joint of the wearer proximate the second end.

17. The method of claim 16, wherein seating at least one tooth of the patient onto the tubular member comprises seating the at least one tooth in a channel of the tubular member, the channel orthogonal to a primary axis of the tubular member.

18. The method of claim 17, further comprising selecting the oral procedure apparatus from a plurality of oral procedure apparatuses, each having a channel of different dimensions, such that the channel securely admits the at least one tooth of the wearer.

* * * * *